United States Patent
Doncaster et al.

(10) Patent No.: US 6,548,024 B1
(45) Date of Patent: Apr. 15, 2003

(54) GAS SENSORS

(75) Inventors: Alan Mason Doncaster, Maldon (GB); Terence David Brown, Chelmsford (GB)

(73) Assignee: EEV Limited, Chelmsford (GB)

( * ) Notice: Subject to any disclaimer, the term of this patent is extended or adjusted under 35 U.S.C. 154(b) by 0 days.

(21) Appl. No.: 09/261,503

(22) Filed: Mar. 3, 1999

(30) Foreign Application Priority Data

Mar. 4, 1998 (GB) ............................................. 9804590

(51) Int. Cl.[7] .................... G01N 30/96; G01N 31/12; G01N 27/00; G01N 19/10; G01N 30/04; G01N 30/02; G01N 27/416; G01N 33/497; G01N 7/00; B01L 3/00; G01J 1/48

(52) U.S. Cl. .......................... 422/88; 422/86; 422/94; 422/98; 422/99; 436/151; 73/23.2; 73/23.31; 73/23.4; 73/23.42

(58) Field of Search ............................. 422/88, 98, 86, 422/94, 99; 436/151; 73/23.2, 23.31, 23.4, 23.42

(56) References Cited

U.S. PATENT DOCUMENTS

| | | | | |
|---|---|---|---|---|
| 3,960,495 A | * | 6/1976 | Tantram | |
| 4,115,068 A | * | 9/1978 | Joslyn | ........................ 422/56 |
| 4,134,818 A | * | 1/1979 | Pebler et al. | |
| 4,141,800 A | * | 2/1979 | Breuer et al. | ............... 204/1 T |
| 4,172,247 A | * | 10/1979 | Ikeura | |
| 4,227,974 A | * | 10/1980 | Petersen et al. | ............ 204/1 T |
| 4,259,292 A | * | 3/1981 | Ichinose et al. | .............. 422/98 |
| 4,305,724 A | * | 12/1981 | Micko | |
| 4,410,632 A | * | 10/1983 | Diley et al. | |
| 4,560,585 A | * | 12/1985 | Khilnani | |
| 4,569,826 A | * | 2/1986 | Shiratori et al. | ............... 422/90 |
| 4,633,704 A | * | 1/1987 | Tantram et al. | ................. 73/23 |
| 4,861,557 A | * | 8/1989 | McNally | |
| 5,055,270 A | * | 10/1991 | Consadori et al. | ............ 422/98 |
| 5,225,786 A | * | 7/1993 | Vaughn et al. | |
| 5,368,713 A | * | 11/1994 | Friese et al. | ................. 204/429 |
| 5,423,973 A | * | 6/1995 | Friese et al. | ................. 204/426 |
| 5,445,796 A | * | 8/1995 | Mori | ........................... 422/98 |
| 5,831,145 A | * | 11/1998 | Logothetis et al. | ........... 73/23.2 |
| 5,840,245 A | * | 11/1998 | Coombs et al. | ................. 422/4 |
| 5,859,362 A | * | 1/1999 | Neudorfl et al. | ............. 73/23.2 |
| 5,989,398 A | * | 11/1999 | Young et al. | ................ 204/424 |
| 5,998,012 A | * | 12/1999 | Friese et al. | ................. 428/325 |
| 6,044,689 A | * | 4/2000 | Yoshida et al. | |
| 6,096,560 A | * | 8/2000 | Scripca et al. | .............. 436/164 |
| 6,165,336 A | * | 12/2000 | Maki et al. | ................... 204/415 |
| 6,337,052 B1 | * | 1/2002 | Rosenwasser | |
| 6,344,174 B1 | * | 2/2002 | Miller et al. | ................... 422/98 |
| 2002/0085956 A1 | * | 7/2002 | Miller et al. | ................... 422/94 |

FOREIGN PATENT DOCUMENTS

| | | |
|---|---|---|
| EP | 0094863 | 11/1983 |
| GB | 2068561 | 12/1981 |

* cited by examiner

Primary Examiner—Jill Warden
Assistant Examiner—Brian R Gordon
(74) Attorney, Agent, or Firm—Donald C. Casey, Esq.

(57) ABSTRACT

In a catalytic sensor, a bead is located within a can having an aperture in its front surface. The bead is surrounded by thermally insulating material such as glass fiber and a filter material is arranged between the bead and the aperture in the can. This acts to remove $H_2S$ or other inhibiting gases before they reach the bead and impair its performance. The thermally insulating material allows the filter material to be included whilst still permitting the bead to be operated at a high temperature.

20 Claims, 2 Drawing Sheets

GAS SENSORS

FIELD OF THE INVENTION

This invention relates to gas sensors and more particularly to combustible gas detectors.

BACKGROUND OF THE INVENTION

In a combustible gas detector, a heatable wire filament exhibits a change in resistance occasioned by the change in its temperature which occurs due to the oxidisation of a combustible gas passing over it. Such gas detectors are usually included in a bridge circuit to determine the change in resistance of the wire filament to give an indication of the concentration of the combustible gas. Whilst it is possible to use a naked wire filament, it is also common to use a wire filament which is embedded in a pellet of ceramic material to provide a more rugged structure, such a construction being known as a pellistor gas sensor. Such a pellet typically includes an oxidation catalyst which reduces the temperature at which oxidation of the combustible gas takes place to reduce to prevent evaporation of the wire filament and hence reduce any tendency for the characteristics of the gas detector to change in service.

In one known gas sensor of this type, a gas detector element is contained within an individual can having an aperture therein through which gas is admitted to come into contact with the detector element. The can is in turn included within the outer housing constructed in accordance with safety requirements, as such gas detectors are often required to operate in potentially flammable atmospheres. Usually, a reference element is also included in another individual can within the same housing as the detector element. In some arrangements, the cans may be of the "open" type which an end wall of the can is absent to allow a relatively large volume of gas to come into contact with the detector and reference elements.

A significant disadvantage of this type of gas sensor is that catalyst inhibition may occur caused by hydrogen sulphide ($H_2S$) or other inhibiting gases. When $H_2S$ comes into contact with the detector element, it may react with catalytic material included in the pellet so that the catalytic material is no longer available for reaction with the gas of interest which is to be detected. Also, the reaction of the $H_2S$ with the catalytic material causes sites to be occupied at which gas molecules to be detected should be received. Therefore, this effectively reduces the surface area of the pellet which is capable of reacting with the gas of interest and hence reduces the output signal of the sensor to a level below that which it should read for a particular gas concentration.

The present invention seeks to provide a gas sensor having improved resistance to catalyst inhibition caused by inhibiting gases.

SUMMARY OF THE INVENTION

According to a first aspect of the invention, a gas sensor comprises a catalytic detector element contained in a can having an aperture which admits gas to be sensed and material located within the can which reacts with an inhibiting gas to prevent at least some of it reaching the detector element.

In a gas sensor in accordance with the invention, the material acts as a filter to remove inhibiting gas from the volume of gas within the can so that a reduced amount of inhibiting gas reaches the detector element. The invention offers improved resistance to the inhibiting gas so that a higher more accurate output signal results and also prolongs the useful lifetime of the detector element itself as the catalyst is consumed at a lower rate. In addition, the location of the material within the can gives an additional benefit as the amount of inhibiting gas reaching the material is pre-limited by the aperture in the can through which gas diffuses. Hence the lifetime of the material itself is enhanced.

Advantageously, the material comprises of least one of copper, bronze, brass, silver, lead, tungsten, molybdenum or any combination, alloy or oxide of one or more of them. Material which includes copper or a copper alloy has been found to be particularly effective in removing hydrogen sulphide. In one advantageous embodiment, the material is a bronze sinter. The pore sizes are selected to allow non-inhibiting gas to diffuse through the sinter whilst ensuring that a large percentage of the inhibiting gas reacts with the bronze and preferably the pore size is in the range of 4 to 50 microns. In another arrangement, the material takes the form of a mesh which may, for example, be a regular matrix or irregular such as a wire wool. The material may be provided in other forms, for example, it may be a powder, but this tends to be more difficult to handle during assembly and to keep in position during use of the sensor.

Although the invention arose from considering how to remove hydrogen sulphide from gas to be detected, chlorine may also have an inhibiting effect on certain types of gas sensor. By appropriate choice of the material, this may be removed instead of or in addition to hydrogen sulphide.

In a preferred embodiment, the material is located between the aperture in the can and the detector element. For example, it may advantageously be located across the whole of the can between the aperture and the detector element so that there is no path for gas from outside the can to the detector element except through the material. Preferably, the material is located adjacent the wall of the can having the aperture therein. The material is then supported by the wall whilst ensuring that all gas diffusing towards the detector element also passes through the material. In one advantageous embodiment, the material is located in the aperture. The material may occupy the aperture only or may also extend somewhat into the interior of the can. The latter configuration is preferred as it gives a longer path for the gas through the material and as it allows more material to be included, increasing the time for which it remains effective.

Preferably, thermally insulating means is located between the material and the detector element.

According to a second aspect of the invention, a gas sensor comprises: a catalytic detector element contained in a can; material located in the can which reacts with an inhibiting gas to prevent at least some of it reaching the detector element; and thermally insulating means located between the detector element and the material. In one embodiment, the thermally insulating means is glass fibre. Other substances may be used instead provided they do not significantly impede the passage of gas to be detected and provide some heat insulation. For example, suitable alternatives are alumina, quartz, zirconia, or other refractory oxides, in the form of fibres, wools or sponges.

The inclusion of the thermally insulating means is particularly advantageous as it allows the detector element to operate at high temperatures, to typically 500° C., without heat losses which might otherwise occur via the material for removing the inhibiting gas. In the absence of the thermal insulation, the material may act as a heat sink, causing the detector element to run at a lower temperature and hence be less effective. The glass fibre insulates the detector element from the material, permitting the surface area of the material to be maximised for optimum filtering of the gas without it having a significant effect on temperature control of the detector element. The thermally insulating means has an additional benefit of providing mechanical shock resistance, particularly in regard to the mounting of the detector element, making the whole device more rugged. The thermally insulating means may offer a further benefit in that often during operation, if the pellistor bead comes into contact with organic molecules at high temperatures, it breaks them down into carbon monoxide and water. The water tends to be held in the glass fibre, or other thermally insulating substance, providing a damp atmosphere in the region of the material which reacts with the inhibiting gas, potentially improving its absorbing properties. Also, water retained in the glass fibre may itself act to absorb hydrogen sulphide to some extent.

The second aspect of the invention may be used where the detector element is contained in an open can or a closed can.

Preferably, the gas sensor includes a housing within which the can is housed. In a preferred embodiment, the housing is flameproof, for example, being of stainless steel and also includes another can containing a reference element. The housing may include a sinter flametrap. The sinter flame arrester also limits the amount of gas entering the housing and may thus also extend the lifetime of the sensor.

An advantage of using the invention in both its first or second aspects is that it allows resistance to inhibiting gases to be improved without the need to alter the external structures of the housing or change its materials. Thus, it is not necessary to seek further approvals from safety certification bodies as only internal parts of the gas detector need be altered.

According to a feature of the invention, an arrangement comprises an array of sensors for detecting respective different gases and includes at least one gas sensor in accordance with the invention. During calibration of an array of gas sensors, often, the calibrating gases used will include hydrogen sulphide, and use of the invention for gas sensors included in such an array improves resistance against such gases used in the course of calibration tests.

Another advantage which arises from use of the invention, and particularly where the gas detector includes a closed can having an aperture therein, is that the inclusion of material to react with inhibiting gas and the thermally insulating may improve silicone resistance and hence reduce catalyst poisoning.

BRIEF DESCRIPTION OF THE DRAWINGS

One way in which the invention may be performed is now described by way of example with reference to the accompanying drawings in which.

DESCRIPTION OF THE PREFERRED EMBODIMENTS

Figure 1:
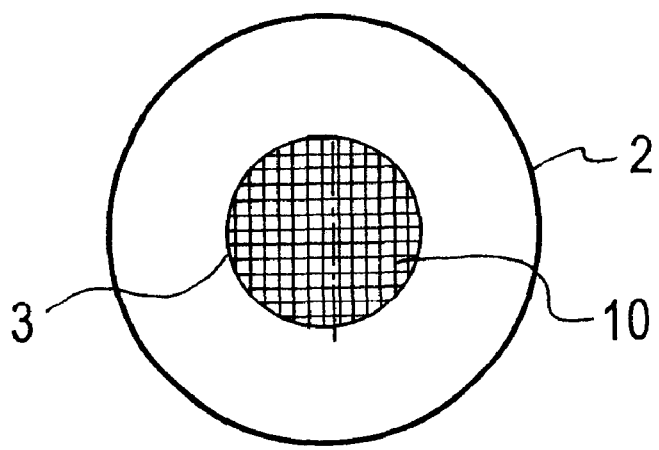
FIGS. 1 and 2 schematically show transverse and longitudinal sections respectively of a detector element enclosed in a can in accordance with the invention.
Figure 2:
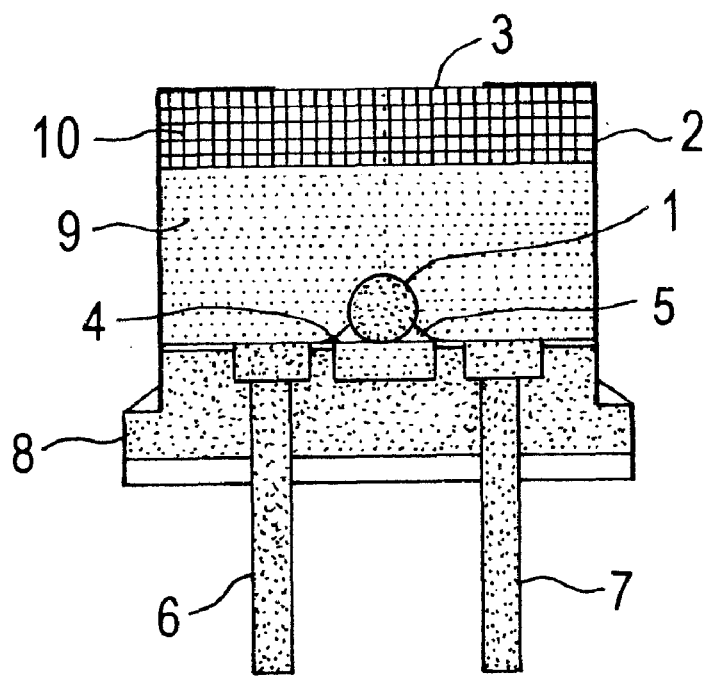

With reference to FIGS. 1 and 2, a silicone resistant catalytic bead 1 is enclosed within an individual can 2 having an aperture 3 in its front surface via which gas to be detected is admitted. The bead 1 is electrically connected via wires 4 and 5 to terminals 6 and 7 which are extensive through a base 8 on which the can 2 is mounted. The interior of the can 2 includes glass microfibre insulating material 9 which provides thermally insulating means around the bead 1 so that it is operable at a relatively high temperature, typically 500° C. A layer of bronze sinter 10 is included within the can 2 being located between the aperture 3 and the bead 1. The bronze sinter 10 reacts with hydrogen sulphide passing through the aperture 3 to prevent at least some of it from reaching the bead 1. However, the bronze sinter does not significantly interfere with the passage of gas which it is wished to detect. The gas to be sensed is any combustible gas or vapour or any combustible mixture of gases or vapours.

In use, electrical current is passed through the bead 1 and any changes in resistance monitored to give an indication of the concentration of gas to be detected.

Figure 3:
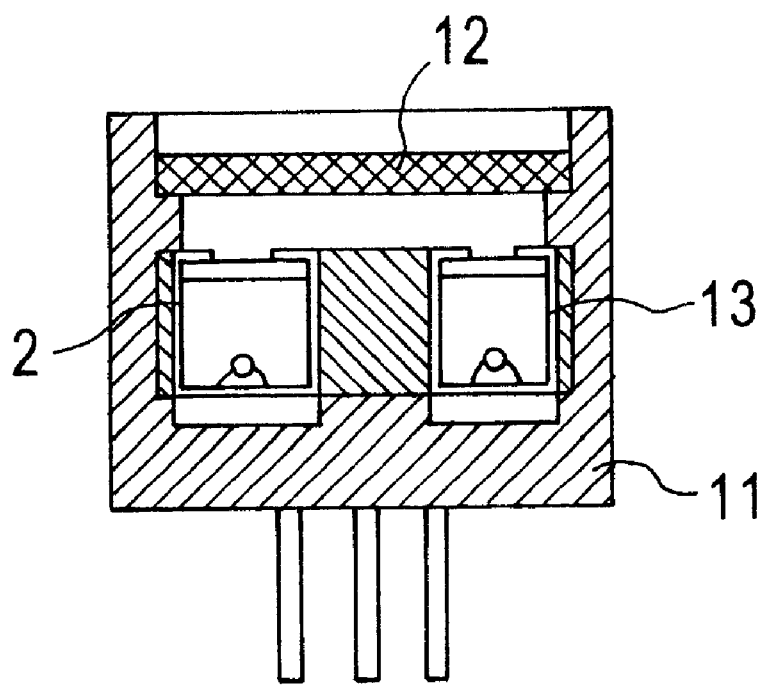
FIG. 3 schematically shows a gas sensor including the detector element of FIGS. 1 and 2.

With reference to FIG. 3, the can 2 of FIGS. 1 and 2 is located within a stainless steel housing 11 having a front aperture with a stainless steel sinter across it to act as a flametrap 12 and via which gas from the ambient atmosphere enters the detector. The housing 11 also includes a second can 13 in which is located another bead 14 which does not include the catalyst and which acts a reference element 14.

Figure 4:
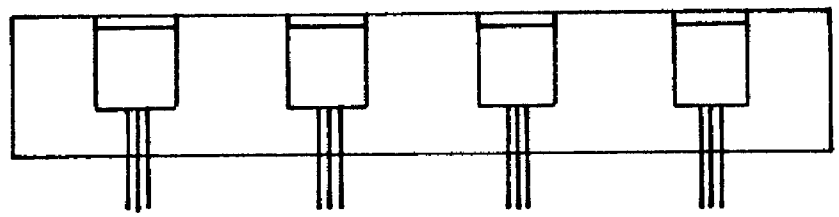
FIG. 4 illustrates a gas sensor array including gas sensors in accordance with the invention.

FIG. 4 illustrates an arrangement of gas sensors in an array, each sensor being configured so as to detect a particular gas or combination of gases. At least one of the gas sensors is as shown in FIG. 3 and incorporates the invention. This ensures that any $H_2S$ used during calibration or other tests does not cause the gas sensor's function to be severely impaired.

We claim:

1. A gas sensor comprising a housing, in which is housed a first can having an aperture therein which admits gas to be sensed; a catalytic detector element contained in said first can; material located within said first can which reacts with an inhibiting gas whereby at least some said inhibiting gas is prevented form reacting with said detector element; wherein said housing houses a second can which contains a reference element; and said first can further comprising thermally insulating means between said material and said detector element.

2. A gas sensor as claimed in claim 1 wherein said material is located between said aperture and said detector element.

3. A gas sensor as claimed in claim 1 wherein said material is located adjacent a wall of said first can in which said aperture is located.

4. A gas sensor as claimed in claim 1 wherein said material is located in said aperture.

5. A gas sensor as claimed in claim 1 wherein said thermally insulating means is glass fiber.

6. A gas sensor as claimed in claim 1 wherein said material comprises at least one of: copper, bronze, silver, lead, tungsten, and molybdenum and any combination, alloy and oxide of one or more of them.

7. A gas sensor as claimed in claim 6 wherein the material is a bronze sinter having a pore size of in the range from 4 microns to 50 microns.

8. A gas sensor as claimed in claim 6 wherein said material is in the form of a mesh.

9. A gas sensor as claimed in claim 1 wherein the inhibiting gas is $H_2S$.

10. A gas sensor as claimed in claim 1 wherein said housing is flameproof.

11. A gas sensor as claimed in claim 1 wherein said housing includes a sinter flametrap.

12. A gas sensor comprising: a housing; a first can housed in said housing; a catalytic detector element contained in said first can; material located in said first can, said material being such that it reacts with an inhibiting gas to prevent, at least some of said inhibiting gas from reacting with said detector element; thermally insulating means located between said detector element and said material; a second can housed in said housing; and a reference element contained in said second can.

13. A gas sensor as claimed in claim 12 wherein said thermally insulating means is glass fibre.

14. A gas sensor as claimed in claim 12 wherein said material comprises at least one of: copper, bronze, silver, lead, tungsten, and molybdenum and any combination, alloy and oxide of one or more of them.

15. A gas sensor as claimed in claim 14 wherein the material is a bronze sinter having a pore size of in the range from 4 microns to 50 microns.

16. A gas sensor as claimed in claim 14 wherein said material is in the form of a mesh.

17. A gas sensor as claimed in claim 12 wherein the inhibiting gas is $H_2S$.

18. A gas sensor as claimed in claim 12 wherein said housing is flameproof.

19. A gas sensor as claimed in claim 12 wherein said housing includes a sinter flametrap.

20. An arrangement comprising an array of gas sensors for detecting respective different gases and including at least one gas sensor comprising: a housing; a first can housed in said housing; a catalytic detector element contained in said first can; material located in said first can, said material being such that it reacts with an inhibiting gas to prevent at least some of said inhibiting gas from reacting with said detector element; thermally insulating means located between said detector element and said material; a second can housed in said housing; and a reference element contained in said second can.

* * * * *